(12) United States Patent
Padilla et al.

(10) Patent No.: US 6,951,053 B2
(45) Date of Patent: Oct. 4, 2005

(54) METHOD OF MANUFACTURING A PROSTHESIS

(75) Inventors: Orlando Padilla, Laguna Niguel, CA (US); Keith Esser, San Diego, CA (US); Joan Zeltinger, Encinitas, CA (US)

(73) Assignee: Reva Medical, Inc., San Diego, CA (US)

( * ) Notice: Subject to any disclaimer, the term of this patent is extended or adjusted under 35 U.S.C. 154(b) by 150 days.

(21) Appl. No.: 10/655,338

(22) Filed: Sep. 4, 2003

(65) Prior Publication Data

US 2004/0127971 A1 Jul. 1, 2004

Related U.S. Application Data

(60) Provisional application No. 60/408,409, filed on Sep. 4, 2002.

(51) Int. Cl.$^7$ .............................. A61F 2/02; B23P 15/00
(52) U.S. Cl. .......................... 29/557; 29/558; 623/1.15; 623/1.16; 623/1.34; 623/1.42; 427/2.24
(58) Field of Search ................... 29/557, 558; 623/1.15, 623/1.16, 1.2, 1.34, 1.38, 1.42, 1.46, 901; 216/52; 427/2.1, 2.24, 2.25; 403/83, 104

(56) References Cited

U.S. PATENT DOCUMENTS

| 5,441,515 A | * | 8/1995 | Khosravi et al. ........... 606/194 |
| 5,618,299 A | * | 4/1997 | Khosravi et al. ............ 623/1.2 |
| 5,733,328 A | * | 3/1998 | Fordenbacher ............. 623/1.16 |
| 6,033,436 A | * | 3/2000 | Steinke et al. ............. 623/1.15 |
| 6,214,037 B1 | * | 4/2001 | Mitchell et al. ........... 623/1.11 |
| 6,224,626 B1 | * | 5/2001 | Steinke ...................... 623/1.16 |
| 6,623,521 B2 | * | 9/2003 | Steinke et al. ............. 623/1.16 |

* cited by examiner

Primary Examiner—Jermie E. Cozart
(74) Attorney, Agent, or Firm—Knobbe, Martens, Olson & Bear, L.L.P.

(57) ABSTRACT

The present invention provides a lumen support prosthesis composed of interlocking radial modules which is fabricated fully assembled from a signal piece shape, without welding or bonding. The prosthesis comprises at least one locking mechanism, allowing for one-way sliding of the radial modules and expansion of the prosthesis from a collapsed state, but inhibits radial recoil from the expanded diameter. The prosthesis may be fabricated from biologically degradable materials which have certain medical advantages.

6 Claims, 13 Drawing Sheets

METHOD OF MANUFACTURING A PROSTHESIS

RELATED APPLICATIONS

This application claims priority under 35 U.S.C. §119(e) to U.S. Provisional Patent Application No. 60/408,409 filed on Sep. 4, 2002.

BACKGROUND OF THE INVENTION

1. Field of the Invention

Preferred aspects of the present invention relate to expandable medical implants for maintaining support of a body lumen and methods of making such implants.

2. Description of the Related Art

An important use of stents is found in situations where parts of the vessel wall or stenotic plaque blocks or occludes blood flow in the vessel. Often, a balloon catheter is utilized in a percutaneous transluminal coronary angioplasty procedure to enlarge the occluded portion of the vessel. However, the dilation of the occlusion can cause fissuring of atherosclerotic plaque and damage to the endothelium and underlying smooth muscle cell layer, potentially leading to immediate problems from flap formation or perforations in the vessel wall, as well as long-term problems with restenosis of the dilated vessel. Implantation of stents can provide support for such problems and prevent re-closure of the vessel or provide patch repair for a perforated vessel. Further, the stent may overcome the tendency of diseased vessel walls to collapse, thereby maintaining a more normal flow of blood through the vessel.

Prior stent designs have been described by Balcon et al., "Recommendations on Stent Manufacture, Implantation and Utilization," European Heart Journal (1997), vol. 18, pages 1536–1547, and Phillips, et al., "The Stenter's Notebook," Physician's Press (1998), Birmingham, Mich.

An important advancement in stent design has been the development of modular sliding and locking expandable stents. See e.g., U.S. Pat. Nos. 6,033,436 and 6,224,626; the entire disclosures of which are incorporated herein in their entireties by reference thereto. These stents comprise a tubular member formed by series of slidably engaged radial modules which compose the wall of the luminal space. These stents are positioned into the appropriate location in a collapsed, small diameter state and then expanded to the diameter necessary to support the vessel. The radial modules comprise locking mechanisms that enables the stent to resist recoil once expanded, locking into its large diameter state. Sliding and locking stents have many advantages over their various predecessors, including a constant longitudinal length, reduced risk of thrombosis and restenosis, greater resistance to recoil after deployment, and greater flexibility.

Previous sliding and locking stent designs required the assembly of numerous links into a tubular form, which, depending on the material used, would require welding or bonding steps in the fabrication process. These steps can be labor and machine intensive. Also, the points of bonding or welding are generally weaker than the materials they hold. Accordingly, there remains a need for a modular slide and lock stent design and methods of manufacture in which the stent is fabricated in a closed-loop and assembled state, without the need of bonding or welding, thereby providing much higher margins of mechanical safety and reliability, while reducing the number of parts and the manufacturing step required.

SUMMARY OF THE INVENTION

A method for manufacturing a prosthesis comprising structurally separate interlocking components is disclosed in accordance with a preferred aspect of the present invention. The method comprises fabricating from a material a contiguous one-piece blank comprising at least a first plane and a second plane and an intersection therebetween; machining, e.g., by cutting or etching, in the first plane a pattern comprising a loop having a slide and lock structure therein, the pattern abutting the intersection at a location; machining, e.g., by cutting or etching, a slot through the second plane at the location, the slot being configured to engage the slide and lock structure, wherein the first and second planes are joined by residual material along the intersection; and removing the residual material to separate the first and second planes, wherein the planes remain slidably coupled to one another.

In a preferred variation of the above method, the contiguous one-piece blank comprises three or four intersecting planes, wherein each plane intersects two other planes. Preferably, the material from which the one-piece blank made is selected from the group consisting of metal, ceramic, polymer, degradable material, and combinations thereof. Where a degradable material is used, it may be selected from the group consisting of polyarylates (L-tyrosine-derived), free acid polyarylates, polycarbonates (L-tyrosine-derived), poly(ester-amides), lysine-containing poly(ester-amides), polyhydroxyalkanoates, poly(propylene fumarate-co-ethylene glycol) copolymer, polyanhydride esters, polyanhydrides, polyorthoesters, silk-elastin polymers, amino acid-containing polymers or corrodible calcium phosphate and magnesium alloys. In another preferred variation, the material may further comprise a biologically responsive or physiologically active substance and/or be at least partially radiopaque.

In another embodiment of the present invention, a prosthesis for support of a body lumen is disclosed. The prosthesis is cut or etched from a one-piece blank in accordance with the method described above. The prosthesis comprises: a tubular member comprising a clear through-lumen, and having proximal and distal ends and a longitudinal length defined there between, a circumference, and a diameter which is adjustable between at least a first collapsed diameter and at least a second expanded diameter, said tubular member comprising: a series of slidably-engaged radial elements, wherein each radial element defines a portion of the circumference of the tubular member; and at least one articulating mechanism which permits one-way sliding of the radial elements from the first collapsed diameter to the second expanded diameter, but inhibits radial recoil from the second expanded diameter.

In another embodiment, an expandable stent for support of a body lumen is disclosed, wherein the stent comprises at least two slidably-engaged radial modules which define a portion of the circumference of a tubular member, wherein the radial modules are interlocked and cannot be separated from one another, and wherein the radial modules have no weld or bond connections.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENT

The current invention relates to a radially expandable stent used to open, expand, or repair a targeted area in a body lumen, which may be fabricated from a single formed shape and is composed of one or more movable, interlocking pieces which are held captive in a closed loop. The stent comprises a tubular member having a length in the longitudinal axis and a diameter in the radial axis, of appropriate size to be inserted into the body lumen. The length and diameter of the tubular member may vary considerably for deployment in different selected target lumens depending on the number and configuration of the structural components, described below. The tubular member is adjustable from a first collapsed diameter to at least a second larger expanded diameter. One or more locking mechanisms are incorporated into the tubular member whereby recoil (i.e., collapse from an expanded diameter to a more collapsed diameter) is minimized, preferably to less than about 5%.

The tubular member in accordance with some embodiments has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials ranging from less than about 0.006 inches for plastic and degradable materials to less than about 0.002 inches for metal materials) and flexible (e.g., less than about 0.01 Newtons force/millimeter deflection) to facilitate delivery to small vessels and through tortuous vasculature. The thin walled design will also minimize blood turbulence and thus risk of thrombosis. The thin profile of the deployed tubular member in accordance with some embodiments also facilitates more rapid endothelialization of the stent.

Stent Configuration and Assembly

Figure 1:
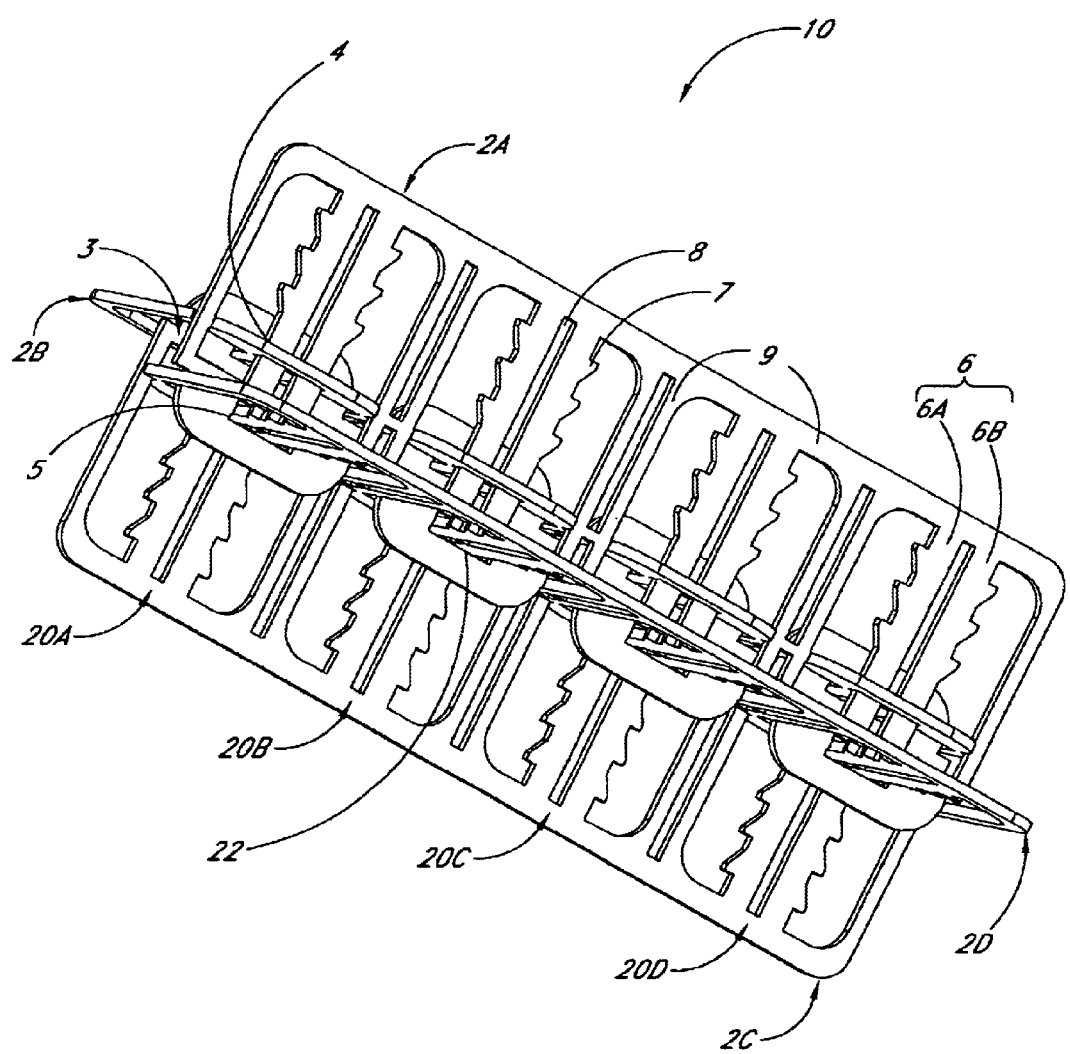
FIG. 1 is a perspective view of an embodiment of a stent with four radial modules wherein each radial module has the same structure.

Referring to FIG. 1, the tubular member 10 comprises at least two, and more preferably three or four (as illustrated), identical interlocking radial modules 2(A–D), which intersect to define a luminal space 3. Each radial module is slidably engaged with at least one other radial module at two locations. See for example module 2A articulating with module 2B at location 4 and module 2D at location 5. Here, the first radial module 2A is engaged with the second radial module 2B at the first location 4 such that the second module may slide in the dimension of the length of the first radial module. The first radial module 2A is also engaged with a third radial module 2D such that the third radial module 2D is in a fixed position in terms of the dimension of the length of the first radial module 2A, but may slide in an intersecting plane, moving above or below the plane of the first radial module.

In one embodiment (shown from various perspectives in FIGS. 1–3), each radial module (see e.g., 2C) comprises four longitudinally disposed and connected radial elements (20A–D). In other embodiments, a radial module may comprise from 1 to 10 radial elements, more preferably from 2–8 radial elements, and most preferably, from 3 to 4 radial elements. Each radial element comprises at least one rib element 6 with at least one tab 7, preferably a plurality of tabs, which articulate within a slot 22 in another, slidably engaged radial element from an intersecting radial module, to create a locking mechanism, allowing the slidably engaged radial elements to slide and lock into at least one fixed position with respect to one another. In the illustrated embodiment, rib elements 6 are paired (6A and 6B) within the radial elements. The paired rib elements (6A and 6B) may be separated from one another by an open channel 8 which may be configured in a preferred embodiment to allow each member of the pair to deflect inward to the other.

In the illustrated embodiment (FIGS. 1–3), each radial element (e.g., 20A) is separated from its longitudinally adjacent radial element (e.g., 20B) by a frame element 9. The tabs 7 on the rib elements 6A and 6B extend outward from the open channel 8. The rib elements 6A and 6B from one radial module are slidably engaged within slots 22 in the intersecting radial modules (e.g., 2A and 2B). When the luminal space 3 is expanded, the tabs 7 on the paired rib elements are depressed when passing through the slot 22, and then spring out, thereby preventing the slidably engaged rib from recoiling back toward a more collapsed configuration. The tabs may be evenly or unevenly distributed along the rib elements.

Figure 3:
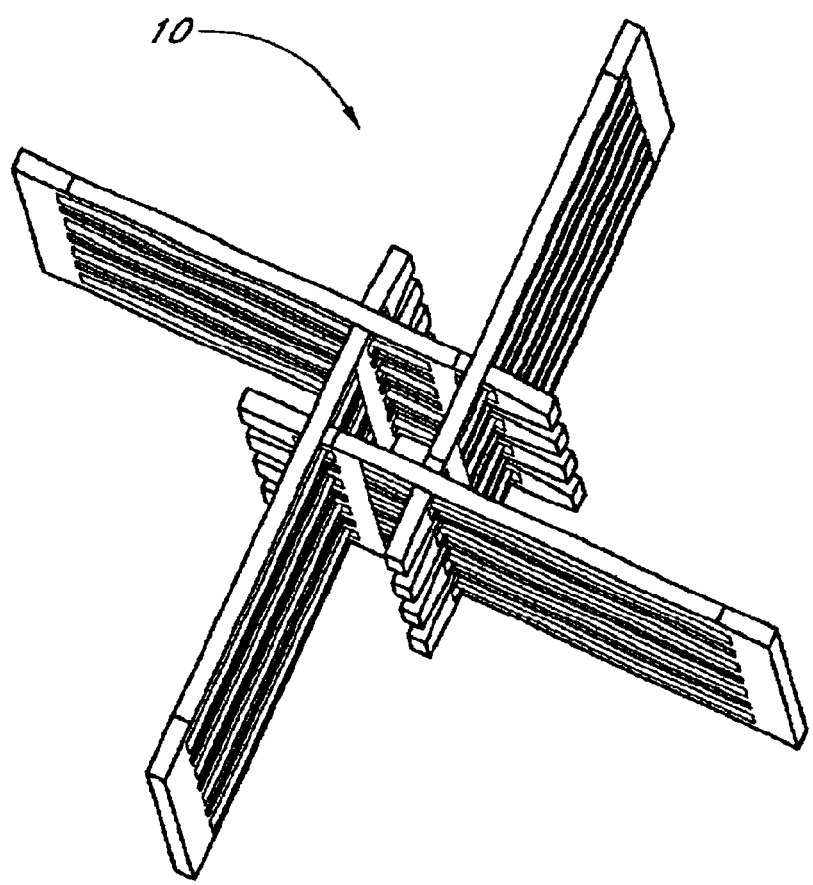
FIG. 3 is a third perspective view of an embodiment of a stent with four radial modules wherein each radial module has the same structure.
Figure 4:
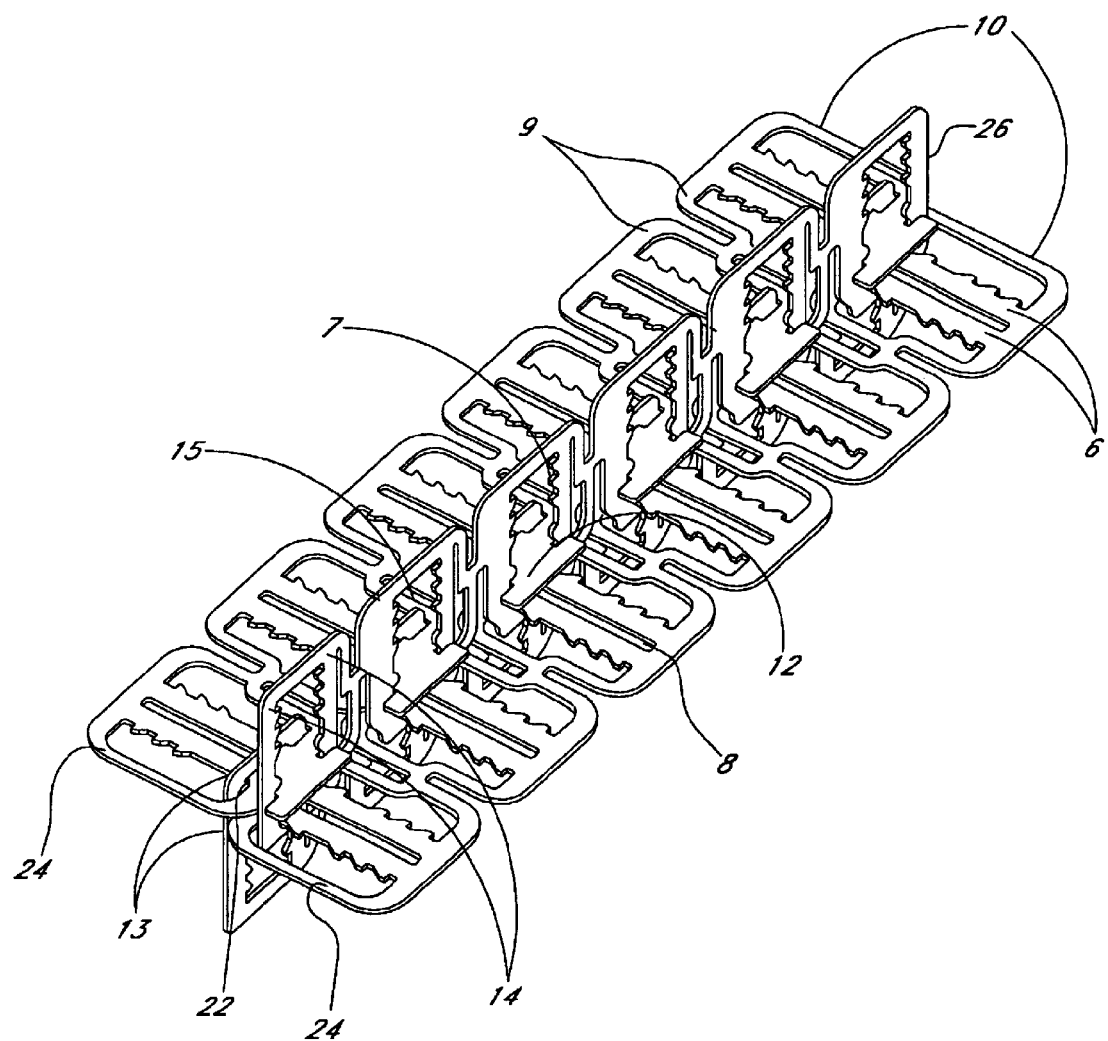
FIG. 4 is a perspective view of an embodiment of a stent with four radial modules, wherein two different types of radial modules are employed.

In another embodiment, FIG. 4, rather than identical radial modules, two different types of radial modules are employed, alpha 24 and beta 26 modules. The alpha radial modules 24, similar those illustrated in FIGS. 1–3, comprise a series of longitudinally connected radial elements, each comprising rib elements 6, shown in pairs separated by an open channel 8, wherein each radial element is surrounded by a frame element 9. Rib elements 6 on alpha modules 24 have at least one tab 7 which serves as a stop that permits one-way sliding of the rib elements within a receiving slot 22 in an adjacent, slidably-engaged radial element in an intersecting beta module. Together the tabs on rib elements on alpha modules and the receiving slots in beta modules constitute a locking mechanism that permit only one-way (expansion) sliding. The alpha radial modules further comprise an engagement member 12 with an engagement groove 13 that interacts with the beta radial modules 26. The beta radial modules may comprise pairs of rib elements 14 having tabs 7 directed toward the space between the rib elements, and thereby defining two sides of an engagement space 15. The engagement member of a first alpha radial module 24 is slidably engaged within the engagement space of a beta radial module 26. The interaction of the engagement grooves 13 with the tabs 7 on the sides of the engagement space 15 constitute another locking mechanism that prevents recoil of the stent once expanded.

In another design variation (not separately illustrated), the tubular member 10 may comprise identical radial modules all have a beta module 26 configuration, wherein each beta module has an engagement member 12 and engagement groove 13, like that shown on alternate alpha modules in FIG. 4.

Figure 5:
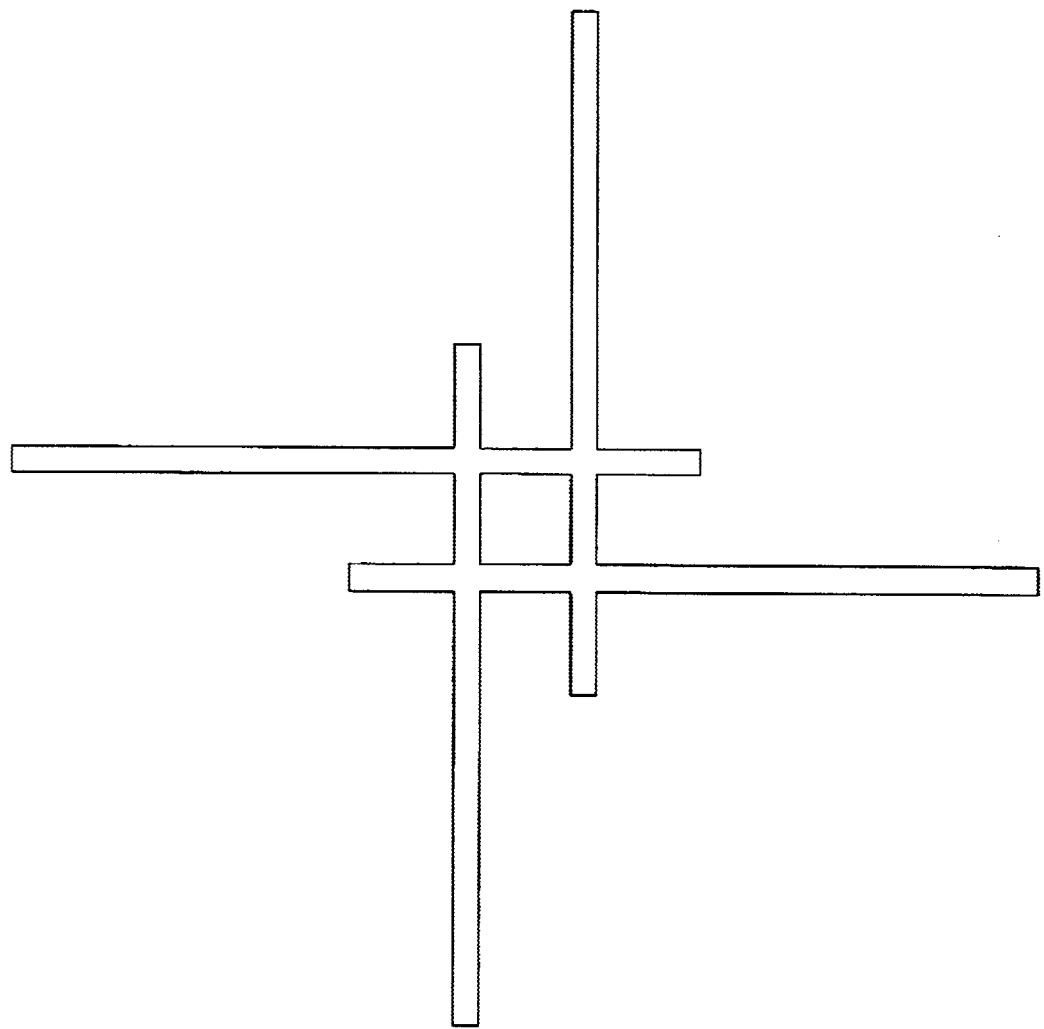
FIG. 5 is a plane view of an extrusion pattern suitable to produce a blank that can be cut or etched to form a stent with four radial modules.
Figure 6:
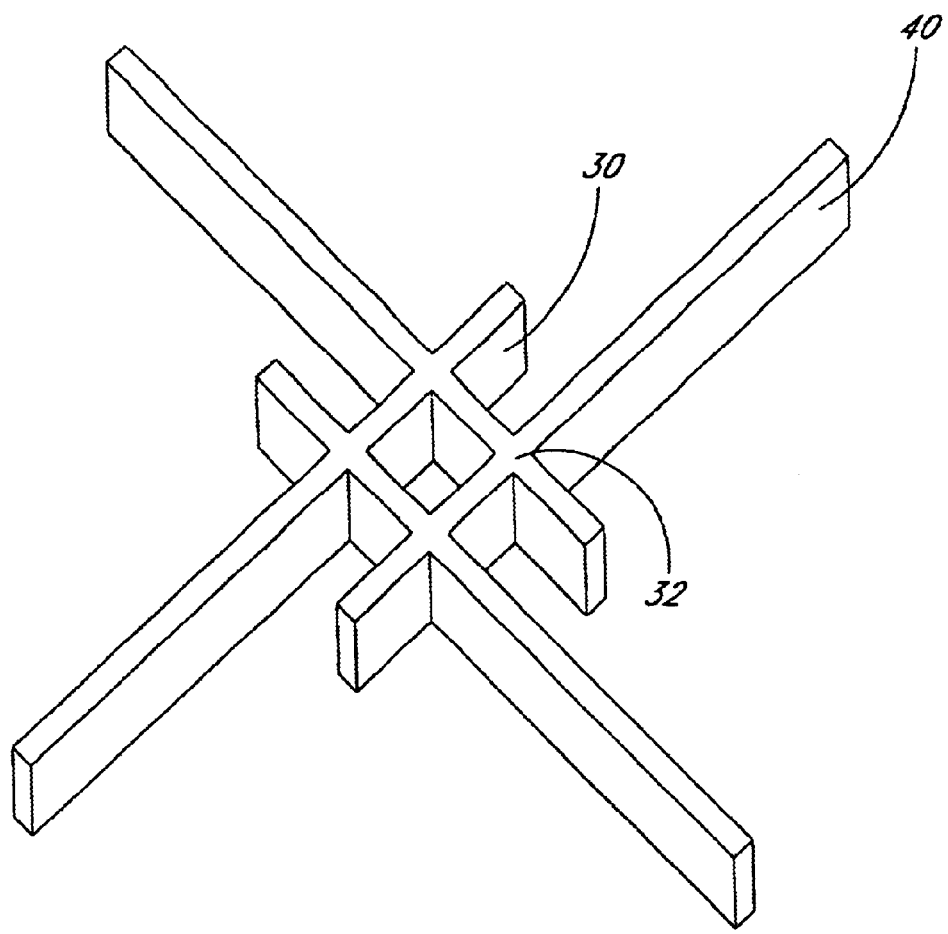
FIG. 6 is a perspective view of a blank suitable for producing a stent with four radial modules.
Figure 7:
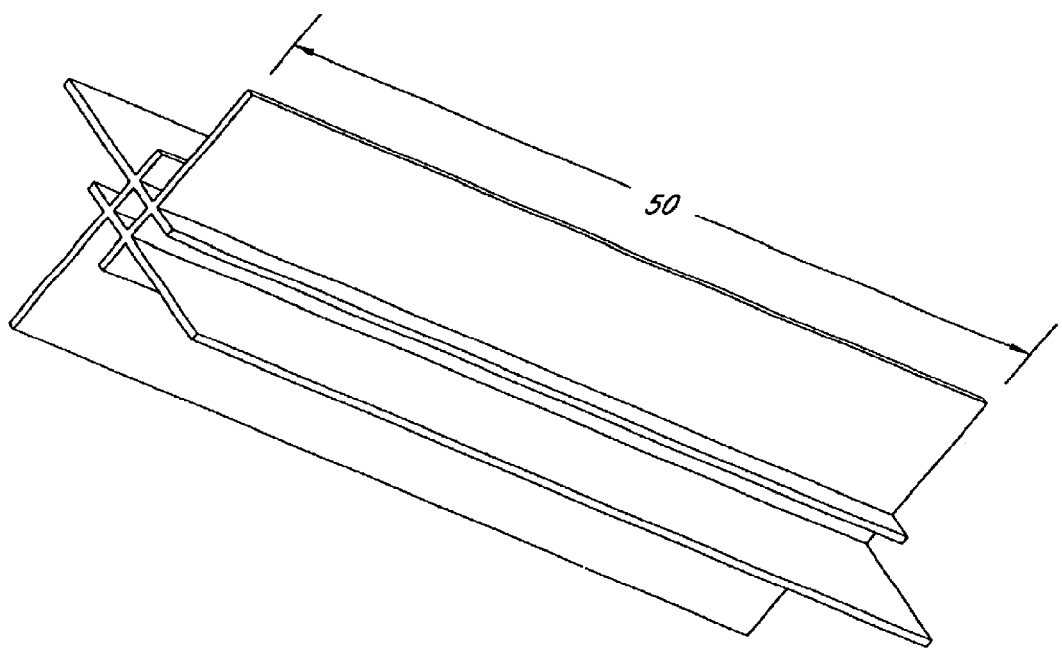
FIG. 7 is a perspective view of another blank suitable for producing a stent with four radial modules.
Figure 9:
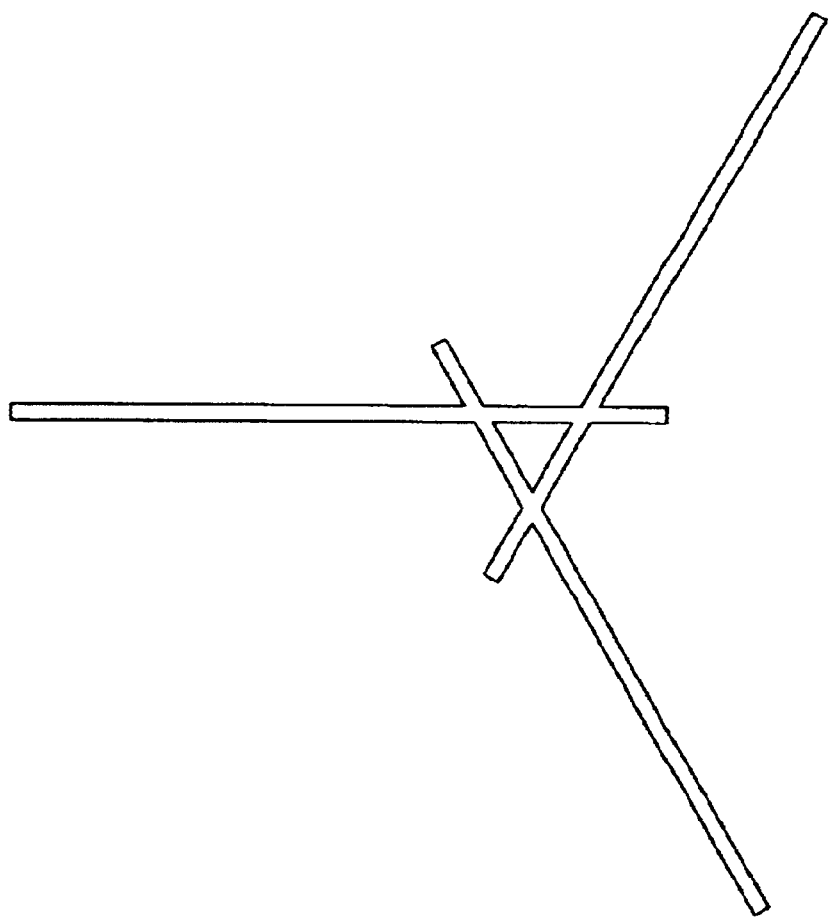
FIG. 9 is a plane view of an extrusion pattern suitable to produce a blank that can be cut or etched to form a stent with three radial modules.
Figure 10:
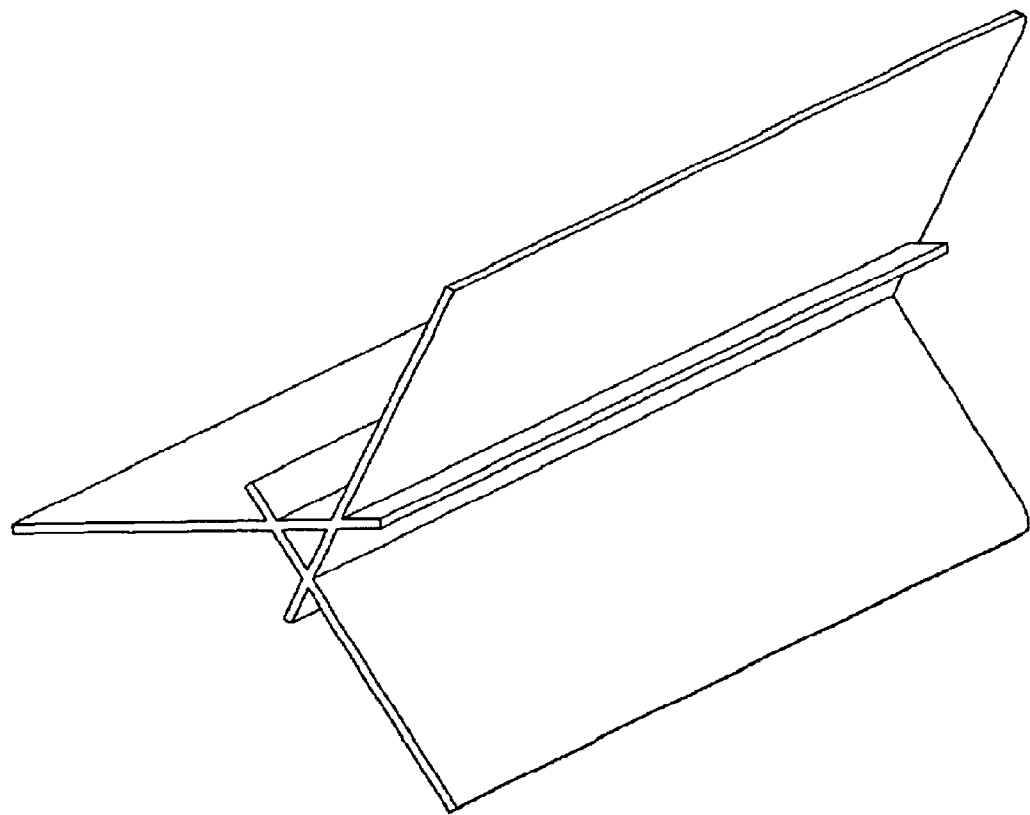
FIG. 10 is a perspective view of a blank suitable for producing a stent with three radial modules.
Figure 11:
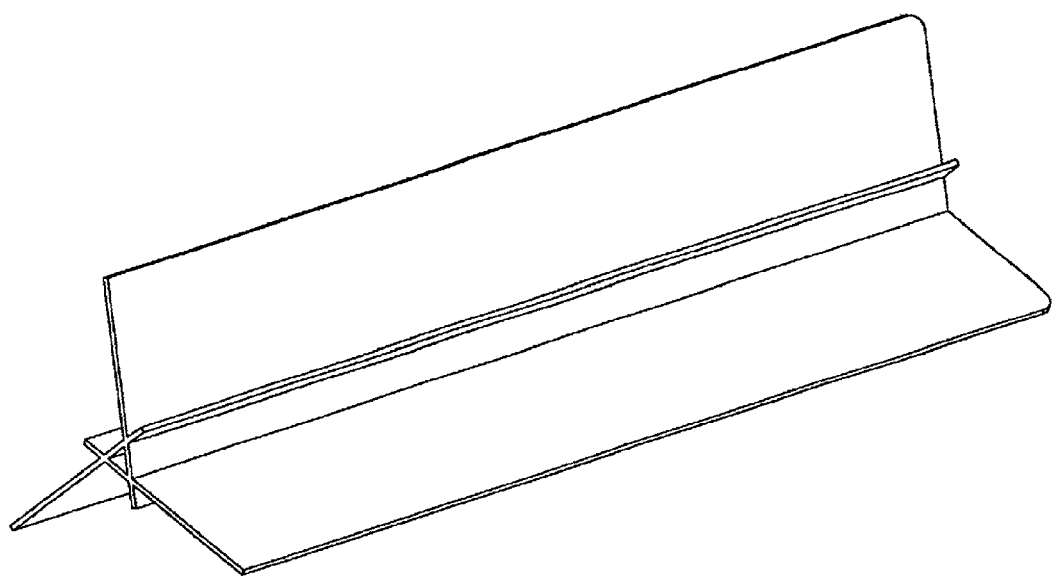
FIG. 11 is a perspective view of another blank suitable for producing a stent with three radial modules.

With reference to FIGS. 5–7, there different perspectives of plan views of an extrusion pattern suitable for producing a solid blank that can be cut or etched to form a stent having four radial modules. Different perspective plan views of an extrusion pattern suitable for producing a solid blank that can be cut or etched to form a stent comprising three radial modules are shown in FIGS. 9–11. The radial modules can be cut or etched in accordance with preferred modes of the invention so that they are all identical (e.g., as shown depicted in FIGS. 1–3, or as described above with respect to the modified beta configuration modules), they can alternate between alpha and beta modules, or they can exhibit any slide and lock articulating structure that may be amenable to cutting or etching from a single piece shape or monolithic material blank. Blanks comprising four modules (FIGS. 5–7) are preferably cut or etched into either identical or alternate module configurations. Blanks comprising three modules (FIGS. 9–11) are preferably cut or etched into identical module configurations. Details of the manufacturing methods are described below.

The structure of the frame elements can be altered to design stents with different degrees of flexibility and support along the length and circumference of the tubular member. It is possible to alter the flexibility of the stent though a variety of means including, but not limited to, the variation in the distance between rib elements, alteration in material thickness, and the incorporation of flexible joint structures. It is also possible to increase the flexibility of the tubular member by designing and cutting a radial module such that the frame element is not continuous over the entire length of the tubular member, thus replacing a radial module with several shorter radial modules all in the same plane. The tubular structure of such an embodiment would be maintained by staggering the points of non-continuity along the circumference and length of the tubular member. Discontinuous frame elements would also facilitate variation in the expanded diameter along the length of the tubular member. Accordingly, the stent may exhibit a tapered configuration with its deployed state, having a larger diameter at one end with progressive or step-wise decreases in modular expanded diameter moving toward the other end of the stent.

Another variation includes varying the locking mechanism and rib element configurations so as to produce increasing friction with progressive expansion. This may also be achieved by incorporating expansion resistors into the stent. This variation may facilitate uniform expansion of all radial elements within the tubular structure.

In another variation, the stent may be used in combination with a covering or sheath to provide a vessel graft, for example, in the treatment of an aneurysm. Materials and methods of making vessel grafts (stent and sheath) incorporating the stent design of embodiments of the invention are described in detail below.

Materials

Preferred materials for making the stents of the present invention include 316 stainless steel, tantalum, titanium, tungsten, gold, platinum, iridium, rhodium, cobalt chrome and alloys thereof. Also shape memory alloys such as Nitinol may be used in accordance with the present invention. Preferred materials also include ceramics.

Degradable biomaterial stents may improve the long-term clinical efficacy for the patients. A completely degradable, drug-eluting stent that resides in the vessel for several months after deployment will be effective in controlling restenosis. Accordingly, the present invention encompasses stents having the sliding and locking geometry described above, wherein the stent components are made from a functional biomaterial.

Generally, the usefulness of a stent past 2–4 months is questionable, as "instent" restenosis is difficult to treat. To address this problem, a stent can be made out of biodegradable materials in order that the stent may be absorbed after it has served its usefulness.

It is believed that there is a need for short-term intervention since the majority of cardiac events occur in the first 6 months, including in-stent restenosis. The permanency of metal stents prevents re-stenting of the same area due to excessive buildup of stent structure. With long lesions and full coverage, metal stents can also preclude surgical re-intervention. The ideal implant: (1) mimics the tissue it is designed to replace in size, shape, and material consistency; (2) neither is disposed to infection nor evokes a foreign body response; (3) is a temporary prosthesis that takes on characteristics of the natural tissue as it disappears; and (4) is a biocompatible implant that has a smooth surface to minimize the risk for thrombus formation and macrophage enzyme activity.

Degradable stents have the potential to perform more like an ideal implant. Degradable stents that integrate seamlessly with the living host tissue may improve tissue biocompatibility due to their temporary residence. With the initial strength to secure the diseased tissue, such stents may eliminate the concern for product migration over time and long-term product failure. They may also minimize time, costs, and complications associated with re-intervention of specific and neighboring sites. Degradable stents have a clear advantage over metal stents in that they can dose the diseased tissue with a drug; compared to drug coated metal stents, degradable stents can hold higher volumes of therapeutic agents and dose the tissue over a longer period of time.

Unlike restenosis after angioplasty, in-stent restenosis is a consequence almost entirely of tissue hyperplasia, occurring principally at the points where the stent's struts impinge upon the artery wall. Placement of an excessively stiff stent against the compliant vessel creates a mismatch in mechanical behavior that results in continuous lateral expansile stress on the arterial wall. This stress can promote thrombosis, arterial wall thinning, or excessive cellular proliferation. Hence, polymeric biomaterials, which are more flexible, may minimize the pathology and are more likely to approximate the mechanical profile of the native tissue.

The intact internal elastic lamina (IEL) of a healthy artery serves as an effective barrier to (1) protect the underlying smooth muscle cells (SMC) from exposure to mitogens that induce hyperplasia, and (2) prevent exposure to monocytes or lipid-filled macrophages and circulating elastin peptides that promote hard plaque formation and narrowing of the artery. A biomaterial stent may minimize progression of disease states by mimicking the barrier functions of the IEL: (1) by delivering a cell-cycle inhibitor to counteract the affects of mitogens, and (2) by serving as a temporary physical barrier to the trafficking immune cells.

In the natural disease states, arteriostenosis and atherosclerosis, arteries can have a compromised or structurally discontinuous IEL. The cause of the discontinuity is largely unknown. Elastases, circulating elastin peptides, and elastin receptors may play a pivotal role along with denudation of the endothelium. The combination of a biomaterial with a stent design which has no recoil can minimize the need to oversize the vessel and thereby minimize the injury to the vessel. In addition the stent surface can serve as an anchorage site for formation of an endothelial lining, the gatekeeper to blood elements and circulating molecules.

It is estimated that pharmacological interventions for restenosis need to occur continuously for 2–4 weeks following angioplasty or stent implantation. It is also estimated that a polymer stent can deliver a drug dose that is ten times higher than can be achieved by systemic delivery. Accordingly, if a cell cycle inhibitor was released from a polymeric degradable stent, optimal long-term patency in the diseased vessel may be achieved.

In one mode of the degradable stent of the present invention, the stent matrix may be formulated so as to release a pharmacologic agent. Mechanical treatment of diseased vessels by angioplasty and stenting can further damage the arterial wall. Ironically, each of these practices can promote thrombus formation and restenosis associated with reocclusion within 6- to 24-months post-procedurally. These inadequate clinical outcomes are the impetus for development of many counteractive therapies. Some new treatments for the reduction restenosis include the use of radioisotopes, Paclitaxel and Rapamycin, all of which inhibit vascular cell proliferation.

In one embodiment, the mechanical properties of the degradable biomaterial are selected in accordance with the present invention to exhibit at least one, and preferably more, of the following characteristics: (1) resist failure due to the multiaxial stress-strain behavior of native arteries; (2) retain radial and structural strength until the vessel has completely healed; (3) degrade via hydrolytic or enzymatic degradation preferably with surface erosion whereby the implant degrades uniformly and maintains its original shape as it degrades; (4) maintains favorable hemodynamics; (5) exhibits a hydrophilic, negatively charged, smooth and uniform surface with a low critical surface tension; (6) supports endothelialization; (7) is nontoxic and eliminated from the body safely, i.e., no systemic effects; and (8) includes an anti-restenosis pharmacological agent. The pharmacologic agent may be a cell-cycle inhibitor that inhibits SMC proliferation, allows for favorable early and late remodeling, and that is stable in the biomaterial. The combination of the degradable biomaterial and the pharmacologic agent preferably provide dosing of the lesion for up to twenty-four weeks, depending upon the mechanism of action of the selected pharmacological agent.

Degradable plastic or natural (animal, plant or microbial) or recombinant materials in accordance with one aspect of the present invention may include polydepsipeptides, nylon copolymides, conventional poly(amino acid) synthetic polymers, pseudo-poly(amino acids), aliphatic polyesters, such as polyglycolic acid (PGA), polylactic acid (PLA), polyalkylene succinates, polyhydroxybutyrate (PHB), polybutylene diglycolate, and poly epsilon-caprolactone (PCL), polydihydropyrans, polyphosphazenes, polyorthoesters, polycyanoacrylates, polyanhydrides, polyketals, polyacetals, poly($\alpha$-hydroxy-esters), poly(carbonates), poly (imino-carbonates), poly($\beta$-hydroxy-esters), polypeptides, and their chemical modifications and combinations (blends and copolymers) and many other degradable materials known in the art. (See e.g., Atala, A., Mooney, D. Synthetic Biodegradable Polymer Scaffolds. 1997 Birkhauser, Boston; incorporated herein by reference).

In one preferred mode, the degradable materials are selected from the group consisting of poly(alkylene oxalates), polyalkanotes, polyamides, polyaspartimic acid, polyglutarunic acid polymer, poly-p-diaxanone (e.g., PDS from Ethicon), polyphosphazene, and polyurethane.

In a more preferred mode, the degradable materials are selected from the group consisting of poly(glycolide-trimethylene carbonate); terpolymer (copolymers of glycolide, lactide or dimethyltrimethylene carbonate); polyhydroxyalkanoates (PHA); polyhydroxybutyrate (PHB) and poly(hydroxybutyrate-co-valerate) (PHB-co-HV) and copolymer of same; poly(epsilon-caprolactone) and copolymers (e.g., lactide or glycolide); poly(epsilon-caprolactone-dimethyltrimethylene carbonate); polyglycolic acid (PGA); and poly-L and poly-D(lactic acid) and copolymers and additives (e.g., calcium phosphate glass) and lactic acid/ethylene glycol copolymers.

In a most preferred mode, the degradable materials are selected from the group consisting of polyarylates (L-tyrosine-derived) or free acid polyarylates, polycarbonates (L-tyrosine-derived, including PDPEC or PDTEC), poly(ester-amides), poly(propylene fumarate-co-ethylene glycol) copolymer (i.e., fumarate anhydrides), polyanhydride esters (mechanically stronger) and polyanhydrides (mechanically weaker), polyorthoesters, ProLastin or silk-elastin polymers (SELP), calcium phosphate (BIOGLASS), magnesium alloys, and a composition of PLA, PCL, PGA ester commercial polymers used singularly or in any mixture.

Natural polymers (biopolymers) include any protein or peptide. These can be used in a blend or copolymer with any of the other aforementioned degradable materials, as well as with pharmacologic substances, or with hydrogels, or alone. Typically, these biopolymers degrade upon the action of enzymes. Preferred biopolymers may be selected from the group consisting of aliginate, cellulose and ester, chitosan NOCC and NOOC-G), collagen, cotton, dextran, elastin, fibrin, gelatin, hyaluronic acid, hydroxyapatite, spider silk, other polypeptides and proteins, and any combinations thereof.

Additional Material Functionalities

Coatings for degradable and metal stent materials may be selected from the group consisting of hydrogels, such as: NO-carboxymethyl chitosan (NOCC), PEG diacrylate with drug (intimal layer) with second layer without drug (blood flow contact), polyethylene oxide, polyvinylalcohol (PVA), PE-oxide, polyvinylpyrolidone (PVP), polyglutarunic acid polymers, DMSO or alcohols and any combinations thereof.

The addition of radiopacifiers (i.e., radiopaque materials) to facilitate tracking and positioning of the stent could be added in any fabrication method or absorbed into or sprayed onto the surface of part or all of the implant. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, iodine may be employed for its radiopacity and antimicrobial properties. Radiopacity is typically determined by fluoroscope or x-ray film.

In any of the embodiments taught or suggested herein, materials may be used that exhibit clinical visibility by iodine or bromine incorporation or other radiopaque elements, use of iodine- or other-containing contrast agents, materials may be non-resorbable polymers or radiopaque constituents of metal particulates, bands or even liquid gold. Methods for viewing may include, but are not limited to, x-ray, fluoroscopy, ultrasound, MRI, or Imatron Electron Beam Tomography (EBT).

Drugs Incorporated into Stents

Drugs and other bioactive compounds can be incorporated into the degradable matrices themselves or coated on the non-degradable (e.g., metal or ceramic) stent materials, thereby providing sustained release of such compounds at the site of the stent. In addition, degradable biomaterial can be fabricated in various forms and processed into the stent components. Preferred biomaterials would incorporate a pharmaceutical agent blended with the degradable polymer prior to fabricating the stent. The preferred pharmaceutical agent(s) control restenosis (including neointimal thickening, intimal hyperplasia and in-stent restenosis or limits vascular smooth muscle cell overgrowth in the lumen of a stented vessel. Other body applications may require different drugs.

In another aspect of the present invention, the stent biomaterial may also incorporate a hydrogel that acts to prevent adhesions of blood cells, extracellular matrix or other cell types. For instance, NOCC and NOCC-G chitosan. In another aspect, the pharmaceutical agents or hydrogels can be coated onto the surface of the biomaterial singularly or in mixtures or in combination with other binders required to adhere or absorb the pharmaceutical or hydrogel to the biomaterial surface. In addition or in the alternative, the pharmaceutical or hydrogel or genetic material may be incorporated with the biomaterial polymer, microspheres, or hydrogel.

Use of synthetic, natural (plant, microbial, viral or animal-derived) and recombinant forms having selected functions or chemical properties can be mixed with complementary substances (e.g., anti-thrombotic and anti-restenosis substances; nucleic acids and lipid complexes). Pharmacologic agents may also incorporate use of vitamins or minerals. For instance, those that function directly or indirectly through interactions or mechanisms involving amino acids, nucleic acids (DNA, RNA), proteins or peptides (e.g., RGD peptides), carbohydrate moieties, polysaccharides, liposomes, or other cellular components or organelles for instance receptors and ligands.

Pharmaceutical agents may be polar or possess a net negative or positive or neutral charge; they may be hydrophobic, hydrophilic or zwitterionic or have a great affinity for water. Release may occur by controlled release mechanisms, diffusion, interaction with another agent(s) delivered by intravenous injection, aerosolization, or orally. Release may also occur by application of a magnetic field, an electrical field, or use of ultrasound.

A variety of compounds which may be used for coating metallic stents or for incorporating into degradable stent materials have been disclosed by Tanguay et al. Cardio Clin (1994) and Nikol et al. Atherosclerosis (1996); these references are herein incorporated in their entirety by reference thereto. These compounds include antiplatelet agents (Table 1), antithrombin agents (Table 2), and antiproliferative agents (Table 3). Some preferred agents that fall within these classes of compounds are presented in Tables 1–3 (below).

TABLE 1

Antiplatelet Agents

| Compound | Action |
| --- | --- |
| Aspirin | Cyclo-oxygenase inhibition |
| Dipyridamole | Phosphodiesterase inhibition |
| Ticlopidine | Blocks interaction between platelet receptors, fibrinogen, and von Willebrand factors |
| C7E3 | Monoclonal antibody to the glycoprotein Iib/IIIa receptor |
| Integrelin | Competitive glycoprotein IIb/IIIa receptor inhibition |
| MK-852, MK-383 | Glycoprotein IIb/IIIa receptor inhibition |
| RO-44-9883 | Glycoprotein IIb/IIIa receptor inhibition |

TABLE 2

Antithrombin Agents

| Compound | Action |
| --- | --- |
| Heparin | Antithrombin III cofactor |
| Low molecular weight heparin (LMWH) | Inhibition of factor Xa by antithrombin III |
| R-Hirudin | Selective thrombin inhibition |
| Hirulog | Synthetic direct thrombin inhibition |
| Argatroban, efegatran | Synthetic competitive thrombin inhibition |
| Tick anticoagulant peptide | Specific thrombin inhibition |
| Ppack | Irreversible thrombin inhibition |

Additional anti-thrombogenic substances and formulations include endothelium-derived relaxing factor, prostaglandin $I_2$, plasminogen activator inhibitor, tissue-type plasminogen activator (tPA), ReoPro: anti-platelet glycoprotein IIb/IIIa integrin receptor, heparin, polyamine to which dextran sulfate and heparin are covalently bonded, heparin-containing polymer coating for indwelling implants (MEDI-COAT by STS Biopolymers), polyurethaneurea/heparin, hirudin/prostacyclin and analogues, fibrin and fibrin peptide A, lipid-lowering drugs, e.g., Omega-3 fatty acids, and chrysalin (aka TRAP-508) by Chrysalis Vascular Technologies (which is a synthetically manufactured peptide portion of the human enzyme thrombin, responsible for blood clotting and initiating cellular/tissue repair). Chrysalin mimics specific attributes of thrombin by interacting with receptors on cells involved in tissue repair.

Other anti-restenosis substances in accordance with the present invention include INTEGRILIN.RTM. (eptifibatide) by COR Therapeutics (blocks platelet clumping), Resten-NG (NeuGene) by AVI BioPhama (synthetic version of C-MYC oncogene), and Implant Sciences Corp., Biodi-vYsio (phosphorylcholine (PC)) by Abbott Laboratories Inc. and Biocompatibles International PLC, Liposomal Prostaglandin El by Endovasc Ltd. and Collaborative BioAlliance, Adenovirus vectors to carry genes to vascular smooth muscle cells (Boston Scientific Corp and CardioGene Therapeutics Inc.), TAXOL (paclitaxel) by Bristol-Myers Squibb (prevents cell division by promoting the assembly of and inhibiting the disassembly of microtubules), and Rapamycin or nitric oxide. Other drugs include dexamethasone, tranilast, probucol, statins, cilostazol, and low molecular weight variations of heparin.

A variety of compounds are considered to be useful in controlling vascular restenosis and in-stent restenosis. Some of these preferred antiproliferative agents are presented in Table 3 (below).

TABLE 3

Antiproliferative Agents

| Compound | Action |
| --- | --- |
| Angiopeptin | Somatostatin analog (drug is a synthetic version of C-MYC oncogene sequence used to control restenosis) |
| Ciprostene | Prostacyclin analog |
| Calcium blockers | Inhibition of slow calcium channels |
| Colchicine | Antiproliferative and migration inhibition |
| Cyclosporine | Immunosuppressive, intracellular growth signal inhibition |
| Cytarabine | Antineoplastic, DNA synthesis inhibition |
| Fusion proteins | Toxin-bounded growth factor |
| Iloprost | Prostacyclin analog |
| Ketaserine | Serotonin antagonist |
| Prednisone | Steroid hormone |
| Trapidil | Platelet-derived growth factor inhibitor (Inhibits trhomboxane-A2 and a competitive PDGF receptor antagonist.) |
| Resten-NG | drug is a synthetic version of C-MYC oncogene sequence used to control restenosis |

In one preferred embodiment, the anti-restenosis substance is a growth-arresting, lipid-derived bioactive compound selected from the group consisting of ceramide or derivatives thereof, dimethyl sphingosine, ether-linked diglycerides, ether-linked phosphatidic acids and sphinganines. In a more preferred embodiment, the growth-arresting lipid-derived bioactive compound is C6 ceramide, which is described in allowed co-pending U.S. application Ser. No. 09/679,715; which is incorporated herein in its entirety by reference thereto.

Specific therapeutic agents have also been identified which may modulate smooth muscle cell (SMC) proliferation. Since SMC cell proliferation has been implicated in atherosclerotic stenosis as well as post-procedural restenosis, incorporation of such agents may be particularly useful. These include without limitation, regulators of SMC mitosis (e.g., TAXOL, Rapamycin, or ceramide) and stimulators and triggers for extracellular matrix production, such as anti-FGF and TGF-$\beta_1$ strategies, tissue inhibitor metalloproteinases (TIMPs), and matrix metalloproteinases (MMPs).

Various compounds address specific pathologic events and/or vascular diseases. Some of these therapeutic target compounds are summarized in Table 4 (below).

TABLE 4

Specific Therapeutic Target Compounds

| Pathologic Event | Therapeutic Target |
| --- | --- |
| Endothelial dysfunction | Nitric oxide inducer or antioxidants |
| Endothelial injury | Administer VEGF |
| Cell activation & phenotypic modulation | MEF-2 & Gax modulators; NFKB antagonists; cell cycle inhibitors |
| Dysregulated cell growth | E2F decoys; RB mutants; cell cycle inhibitors |
| Dysregulated apoptosis | Bax or CPP32 inducers; Bcl-2 inhibitors; integrin antagonists |
| Thrombosis | IIb/IIIa blockers; tissue factor inhibitors; anti-thrombin agents |
| Plaque rupture | Metalloproteinase inhibitors; leukocyte adhesion blockers |
| Abnormal cell migration | Integrin antagonists: PDGF blockers; plasminogen activator inhibitors |
| Matrix modification | Metalloproteinase inhibitors, plasminogen antagonists; matrix protein cross-linking modifiers |

The therapeutic agents to be bonded to or incorporated within the stent materials of the present invention may be classified in terms of their sites of action in the host. The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-$\alpha$), gamma interferon (interferon-$\gamma$), and Tranilast, which modulate the inflammatory response.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Genetic approaches to control restenosis include without limitation: use of antisense oligonucleotides to PDGFR-$\beta\beta$ mRNA to control PDGF expression; use of antisense oligonucleotides for nuclear antigens c-myb or c-myc oncogenes (Bauters et al., 1997, Trends CV Med); use of antisense phosphorothioate oligodeoxynucleotides (ODN) against cdk 2 kinase (cyclin dependent kinase) to control the cell cycle of vascular SMC (Morishita et al, 1993, Hypertension); use of VEGF gene (or VEGF itself) to stimulate reconstructive wound healing such as endothelialization and decrease neointima growth (Asahara et al 1995); delivery of the nitric oxide synthetase gene (eNOS) to reduce vascular SMC proliferation (Von Der Leyen et al., 1995, Proc Natl Acad Sci); use of adenovirus expressing plasminogen activator inhibitor-1 (PAI-1) to reduce vascular SMC migration and thereby diminish restenosis (Carmeliet et al., 1997, Circulation); stimulation of apolipoprotein A-1 (ApoA1) over-expression to rebalance serum levels of LDL and HDL; use of apoptosis gene products to promote cell death (of SMC) and cytotactic gene products that regulate cell division (tumor suppressor protein p53 and Gax homeobox gene product to suppress ras; p21 over expression); and inhibition of NFKB activation (e.g., p65) to control SMC proliferation (Autieri et al., 1994, Biochem Biophys Res Commun).

Other therapeutic substances that may be useful as stent coatings and/or depot formulations incorporated within degradable stents include: antibodies to ICAM-1 for inhibition of monocyte chemotactic recruitment and adhesion, macrophage adhesion and associated events (Yasukawa et al, 1996, Circulation); toxin based therapies such as chimeric toxins or single toxins to control vascular SMC proliferation (Epstein et al., 1991, Circulation); bFGF-saporin to selectively stop SMC proliferation among those cells with a large number of FGF-2 receptors (Chen et al, 1995, Circulation), suramin inhibits migration and proliferation by blocking PDGF-induced and/or mitogen activated protein kinase (MAPK-AP-1)-induced signaling (Hu et aL, Circulation, 1999); Beraprost Sodium, a chemically stable prostacyclin analogue (PG $I_2$), suppresses intimal thickening and lumenal narrowing of coronary arteries. (Kurisu et al., Hiroshima J. Med Sci, 1997); Verapamil inhibits neointimal smooth muscle cell proliferation (Brauner et al., J Thorac Cardiovasc Surg 1997), agents that block the CD 154 or CD40 receptor may limit the progression of atherosclerosis (E Lutgens et al., Nature Medicine 1999), agents that control responses of shear stress response elements or mechanical stress or strain elements or heat shock genes; and antichemoattractants for SMC and inflammatory cells.

In addition or in the alternative, cells could be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells could also serve as a limited or timed release system. Cells or any origin may be used in accordance with this aspect of the present invention. Further, preserved or dehydrated cells which retain their viability when rehydrated may be used. Native, chemically modified (processed), and/or genetically engineered cells may be used.

It should be understood that all stent edges are preferably smooth and rounded to prevent thrombogenic processes and reduce the stimulation of intimal smooth muscle cell proliferation and potential restenosis. Furthermore, the stent material may be coated with materials which either reduce acute thrombosis, improve long-term blood vessel patency, or address non-vascular issues. Coating materials that may be utilized to reduce acute thrombosis include: parylene; anticoagulants, such as heparin, hirudin, or warfarin; antiplatelet agents, such as ticlopidine, dipyridamole, or GPIIb/IIIa receptor blockers; thromboxane inhibitors; serotonin antagonists; prostanoids; calcium channel blockers; modulators of cell proliferation and migration (e.g. PDGF antagonists, ACE inhibitors, angiopeptin, enoxaparin, colchicine) and inflammation (steroids, non-steroidal anti-inflammatory drugs). Coating materials which may be used to improve long-term (longer than 48 hours) blood vessel patency include: angiogenic drugs such as, Vascular Endothelial Growth Factor (VEGF), adenovirus, enzymes, sterol, hydroxylase, and antisense technology; drugs which provide protection on consequences of ischemia; lipid lowering agents, such as fish oils, HMG, Co-A reductase inhibitors; and others. Finally, drugs that address nonvascular issues such as ibutilide fumarate (fibrillation/flutter), adenylcyclase (contractility), and others, may be applied as stent coatings.

Method of Manufacturing Stent from a Single Piece Shape

Preferred aspects of the present invention further entail the method for producing a stent. In one preferred embodiment, the first step of production is the fabrication of a blank of an appropriate shape (see e.g., FIGS. 5–7 and 9–11). FIGS. 5–7 depict blanks suitable for the production of stents with four radial modules. FIGS. 9–11 depict blanks suitable for the production of stents with three radial modules.

The blank may be produced by extrusion, injection molding, or any other method known in the art for producing a solid shape out of a single material and with a specified form. FIG. 5 shows an extrusion pattern suitable to produce a blank that can be cut to form a stent with four radial modules. FIG. 9 shows an extrusion pattern suitable for producing a blank that can be cut to form a stent with three radial modules. In embodiments with multiple radial modules, the blank is designed to have as many sheets or planes as the number of desired radial modules, with each sheet intersecting one or two other sheets at two locations, so that a tubular geometric shape (which corresponds to the luminal space in the finished stent) is defined by the sheets. In one embodiment, each sheet in the fabricated blank extends beyond the periphery of the central tubular shape on both sides, with one side being longer than the other as illustrated in FIGS. 6 and 7. For example, with reference to FIG. 6, short 30 and long 40 extensions of the sheets should alternate around the circumference of the tubular (or open geometric) shape. With reference to FIG. 7, the blank is preferably fabricated as long as the desired length 50 of the final stent In other embodiments of the present invention, the blank may be fabricated so that the sheets extend minimally beyond the intersections. Thus, it should be understood that the blank can be fabricated at a collapsed diameter of the tubular member (undeployed state), wherein the sheets extend well beyond the intersections 32 as illustrated in FIG. 6, an expanded diameter (deployed state), wherein the sheets extend only minimally beyond the intersections (not shown), or any diameter therebetween. In some embodiments comprising a plurality of modules (sheets), the expanded diameter may be preferred because it provides more room for subsequent cutting of the sheets. It should be understood that the sheets need not be flat, but may be arced or otherwise shaped.

Figure 8:
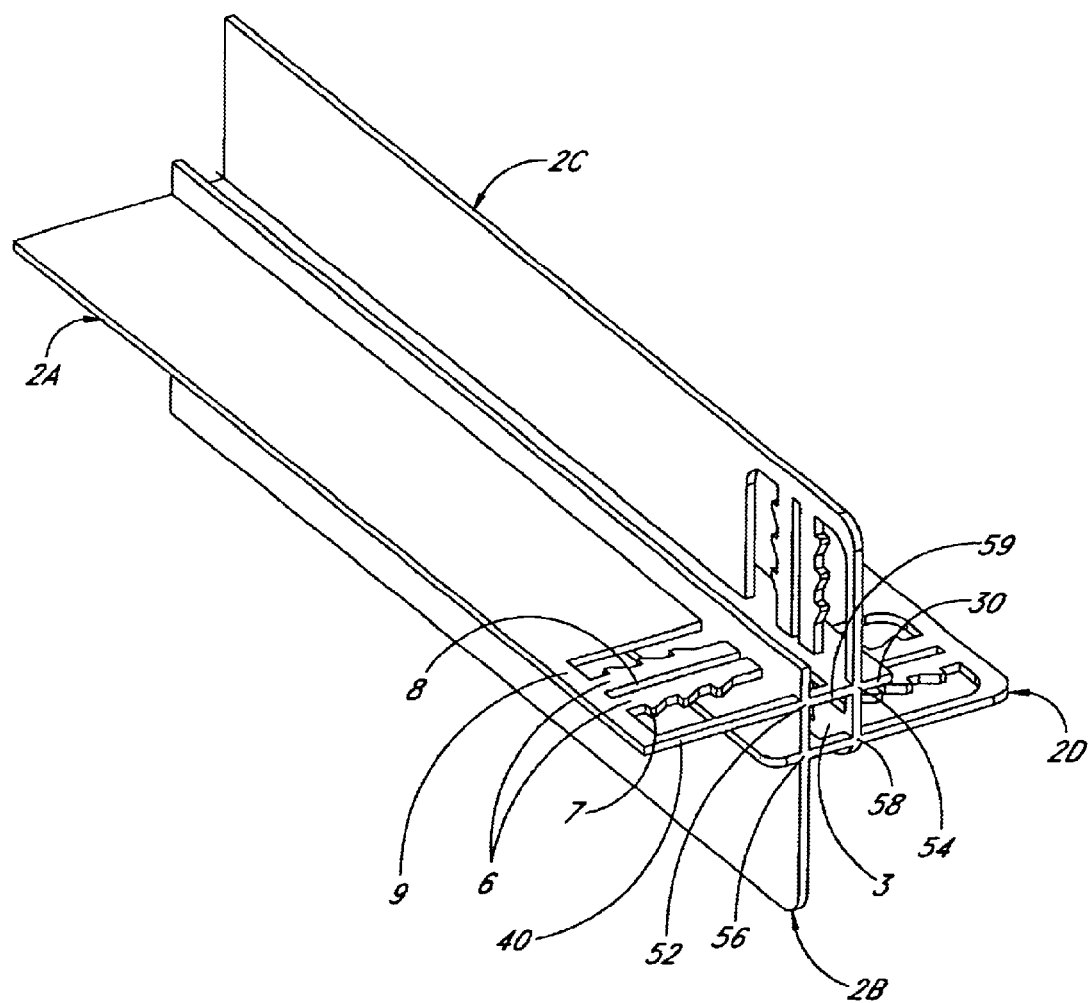
FIG. 8 is a perspective view of an extrusion blank that has been partially cut to reveal the structure of a stent comprising four radial modules.

Once the blank has been fabricated, the next step in the production of the stent is to cut or etch the blank in accordance with the stent design. With reference to FIG. 8, it can be seen that individual sheets in the blank may be cut or etched separately. In one preferred embodiment, the cutting is achieved by first loading the blank onto a machine tool that has at least two degrees of freedom. Excess material that is not specified in the design of the stent is then removed by an appropriate means including lasers, fluid, cutting tools, chemical etching, and the like. During the cutting process it may be necessary to temporarily bend the sheets of the blank so that the cutting means may access the area that is to be cut. The sheets may be alternately bent in opposite directions so that the cutting means may cut between the sheets to form separate radial modules. Finally, the former blank is removed from the tool and any remaining flash is removed from the stent structure.

Figure 2:
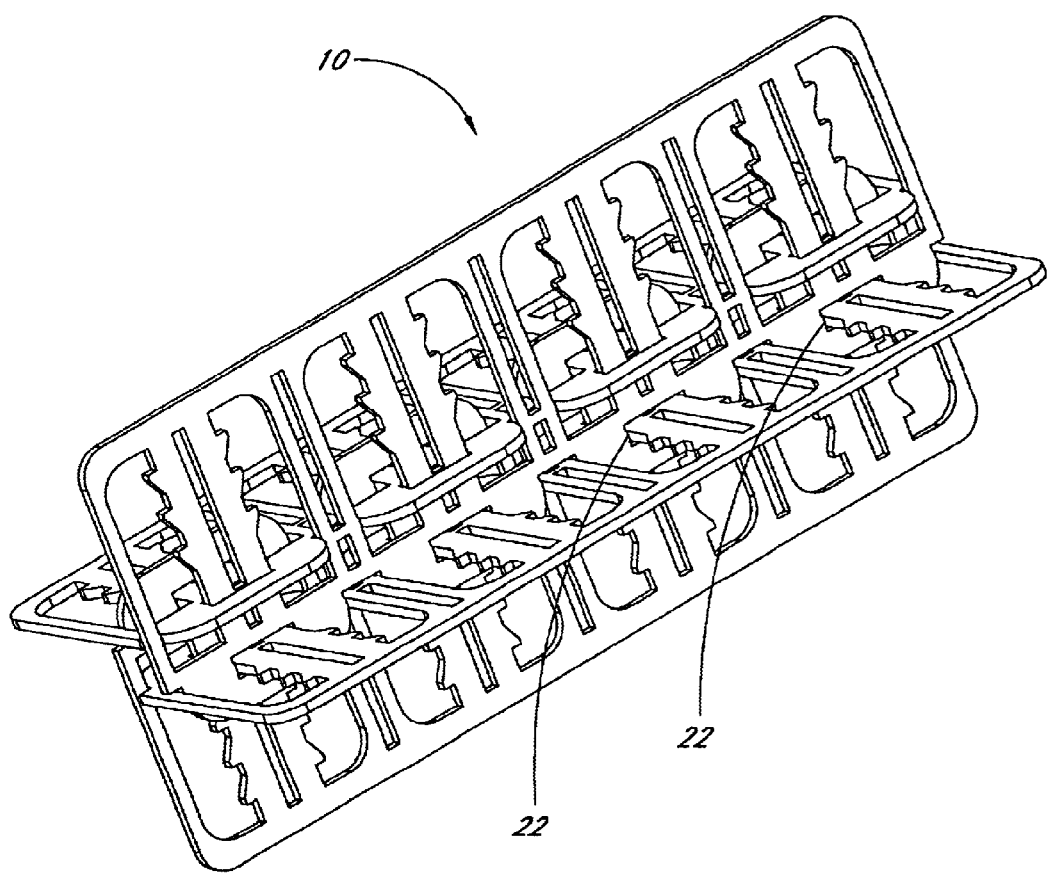
FIG. 2 is a second perspective view of an embodiment of a stent with four radial modules wherein each radial module has the same structure.

FIG. 8 depicts a blank suitable for the production of a stent with four radial modules that has been partially cut or etched to reveal the stent structure, similar to the embodiment shown in FIGS. 1–3. In this embodiment a first sheet 2A intersects with a second sheet 2B and a third sheet 2C along intersection lines (the cross-section of the intersecting points are shown as 52 (intersection of 2A and 2B) and 54 (intersection of 2A and 2C). A forth sheet 2D also intersects with the second 2B and third 2C sheets along intersecting lines (shown in cross-section as points 56 and 58, respectively). The portions of each sheet between these intersections (e.g., wall portion 59) define a central rectangular geometric shape 3. Long 40 and short 30 extensions of the sheets extend from the central geometric shape. Each sheet will be cut to form one radial module. In FIG. 8, the long sheet extension of three of the sheets (2A, 2C and 2D) have been cut or etched to reveal a set of paired ribbed elements 6 with tabs 7, a central channel 8, and a frame element 9.

In order for the rib elements of one radial module (e.g., rib element 6 in sheet 2A) to be slidably engaged with a second radial module (e.g., sheet 2B) in the finished stent, a slot (not shown) is cut in the second sheet 2B such that rib elements 6 from the first sheet 2A separate from the second sheet along the line of intersection, but wherein the rib elements from the first sheet remain moveably engaged within the newly cut slot in the second sheet. Preferably, the slot in the second sheet is cut at approximately a 70–100° angle, and more preferably about a 90° angle, relative to the first sheet. The cutting of this slot constitutes the formation of a first closed loop structure in a radial module of this stent, wherein a structural element from one module is captured (slidably engaged) within a closed loop of another module. A slot is also cut in the first sheet so as to engage the rib elements of the third sheet, thereby generating a second closed loop structure. In this embodiment, slots are cut in all the sheets to allow slidable engagement, without requiring welding or bonding to create the closed loop. Frame elements are also cut such that a frame element from one radial module is not physically continuous with the frame element of an intersecting radial module.

As mentioned above, it may be necessary to bend or deform one or more sheets to allow the cutting means (e.g., laser) access to the material that must be removed. For example, it may be necessary to bend the long sheet extension of the third sheet so that a cutting means may cut a slot in the first sheet such that it will engage the rib elements of the third sheet. Such bending or deformation may occur multiple times. Preferably, residual material is initially left along the intersection between radial modules during the cutting, preventing the radial modules from sliding, so that the stent maintains its initial shape and configuration. Once the structure of the radial modules has been cut out, the residual material is removed, allowing for a stent with articulating components., i.e. allowing the radial modules to be slidably engaged.

Figure 12:
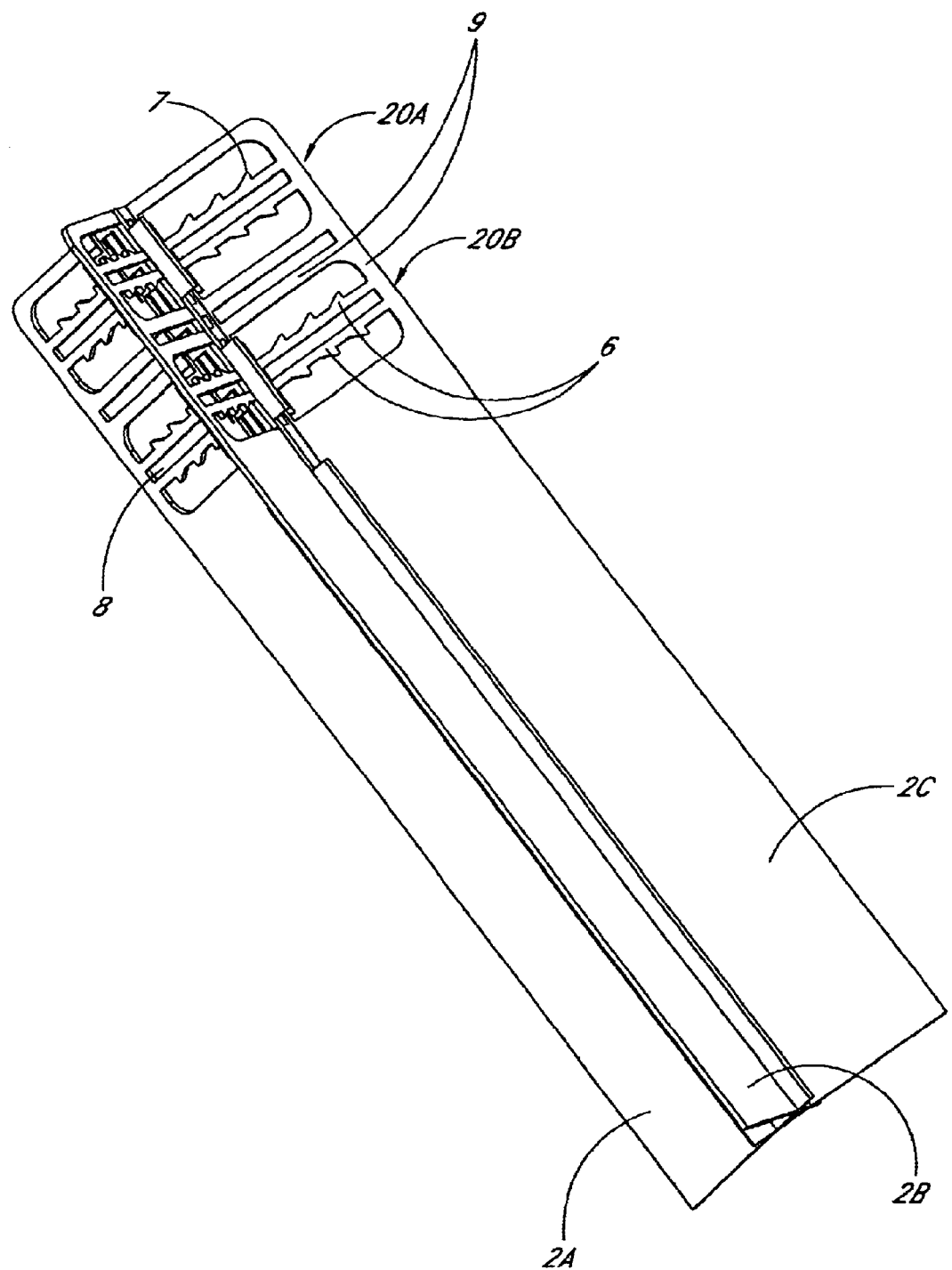
FIG. 12 is a perspective view of an extrusion blank that has been partially cut to reveal the structure of a stent comprising three radial modules.
Figure 13:
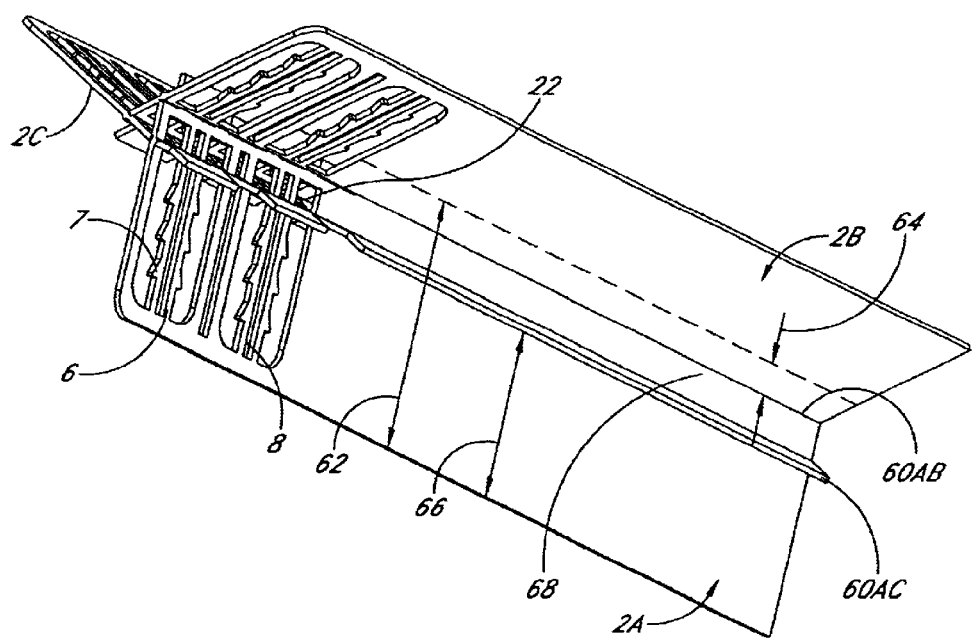
FIG. 13 is a second perspective view of an extrusion blank that has been partially cut to reveal the structure of a stent comprising three radial modules.

FIGS. 12 and 13 depicts a blank suitable for the production of a stent with three radial modules that have been partially cut or etched to reveal the stent structure. In this embodiment a first sheet 2A intersects with a second sheet 2B and a third sheet 2C. With reference to FIG. 12, a pattern, consisting of two longitudinally adjacent radial elements 20A and 20B, has been partially cut or etched into each of the three planes or sheets. Similar to other radial elements described herein, each radial element comprises a rib element 6 (preferably paired, having locking tabs 7 and an open channel 8 between the paired ribs), a frame element 9, and a slot (not shown) to receive the adjacent interlocking plane of sheet. The intersection between any two sheets or planes occurs along a defined line. With reference to FIG. 13, each plane or sheet has two intersections (one with each of the other sheets in the blank) one line of intersection 60AB divides or bisects each plane (2A and 2B) into two distinct areas, a proximal area 62 (in the illustrated case, the long extension of 2A) relative to the intersection 60AB and a distal area 64 (in the illustrated case, the short extension of 2A) relative to the intersection. Another line of intersection 60AC divides each plane (2A and 2C) into two distinct areas, a proximal area 66 and a distal area 68, relative to the intersection 60AC. The proximal area 62 of 2A with respect to intersection 60AB encompasses all of the proximal area 66 of 2A with respect to intersection 60AC. Likewise, the distal area 64 of 2A with respect to intersection 60AB encompasses all of the distal area 68 of 2A with respect to intersection 60AC.

Each sheet will be cut to form one radial module. In FIGS. 12 and 13, the long sheet extensions (proximal areas) of the three sheets have been partially cut or etched to reveal a pattern which forms the slide and lock structure configured to interact with the other radial modules of the prosthesis. In one preferred embodiment, the pattern is cut or etched in the proximal (e.g., 66) and distal (e.g., 68) areas of each plane, leaving that plane joined to its adjacent intersecting plane along the line of intersection (e.g., 60AC). The patterns are cut or etched in the proximal and distal areas (e.g., using a cutting jig having the necessary degrees of freedom), while the one-piece blank is still intact. Subsequently, a slot 22 is cut (e.g., in 2C), preferably at an angle nearly normal (about 90°) to plane 2C, and nearly parallel to 2A, along the line of intersection (e.g., 60AC) to separate the portions of the slide and lock structure (e.g., 6,7,8) of 2A from plane 2C. It should be appreciated that any slide and lock structure may be used in accordance with preferred aspects of the present invention (for example, those disclosed in co-pending U.S. application Ser. No. 09/739,552; which is incorporated herein in its entirety by reference thereto).

It may be desirably to bend proximal and/or distal portions of 2A, 2C or 2B out the way to facilitate cutting or etching the slots. Because the slot 22 is cut in plane 2C at the location where plane 2A intersected and passed through plane 2C, the portions of 2A separate from the previously shared material of 2C, but remain interlocked in a moveably (slidably) engaged manner within the slot 22.

This same procedure of cutting slots is repeated along each line of intersection in each plane (each plane being already cut or etched proximal and distal to the intersection in a pattern configured to provide a slide and lock mechanism), such that open slots are cut or etched thereby creating (in the illustrated embodiment) three distinct, slideably engaged and interlocking radial modules—without the need to weld or bond any additional interlocking structure to any of the modules.

After all of the slots have been formed, the prosthesis can be rolled as is well known in the art. Preferably, a mandrel is placed through the open geometric channel (luminal space 3), and the proximal and distal ends of the radial modules are rolled to form a tubular structure, which is pre-configured to exhibit one-way slide and lock radial expansion. It should be recognized that significant variation in the order by which structures are cut out of the blank is possible. For example, the cutting of a blank to reveal structure may proceed from one end of the blank to the other, make take place as steps that occur across the length of the blank, may comprise completing one radial element before moving on to another, may comprising cutting peripheral or proximal structures before central or distal ones, etc.

Depending on the method used to produce the blank, it is possible that the blank may be created with most of the features of the captured, interlocking design of the stent already formed, requiring only minimal cutting of slots to separate the radial modules into independently moving pieces.

Stent Deployment

Prior to deployment, the portions of the radial modules that are not forming the wall of the luminal space in the collapsed state will be crimped to reduce the effective diameter of the stent. Stents can be deployed in a body lumen by means appropriate to their design. One such method would be to fit the collapsed and crimped stent over an inflatable element of a balloon catheter and expand the balloon to force the stent into contact with the body lumen. As the balloon is inflated, the problem material in the vessel is compressed in a direction generally perpendicular to the wall of the vessel which, consequently, dilates the vessel to facilitate blood flow there through. Radial expansion of the body lumen occurs in several different dimensions and is related to the nature of the plaque. Soft, fatty plaque deposits are flattened by the balloon and hardened deposits are cracked and split to enlarge the lumen. It is desirable to have the stent radially expand in a uniform manner.

A self-expanding stent in accordance with another embodiment of the present invention may be deployed without the use of an inflatable balloon. Instead, the stent may be maintained in its collapsed state on a catheter by a physical restraint, such as an outer sheath corded tie down method or other means. The catheter and stent are advanced as above to the target site, tracking the stent location by fluoroscopy (focusing on the radiopaque elements of the stent). Once at the target site, the stent collapsed around the underlying catheter may be deployed by removing the restraint. For instance, the restraining sheath may be withdrawn, thereby freeing the stent of the physical restraint. Alternatively, the sheath may remain stationary while the collapsed stent and catheter are pushed through the end of the sheath. Regardless of the means of removing the restraint, the stent is then permitted to expand naturally under the influence of its inherent spring force to its second, expanded diameter, bearing against the inner walls of the target passageway.

The stents of the present invention are adapted for deployment using conventional methods known in the art and employing percutaneous transluminal catheter devices. The stents are designed for deployment by any of a variety of in situ expansion means, such as an inflatable balloon or a polymeric plug that expands upon application of pressure. For example, the tubular body of the stent is first positioned to surround a portion of an inflatable balloon catheter. The stent, with the balloon catheter inside is configured at a first, collapsed diameter, wherein a fraction of each radial module composes the wall of the central luminal space and the remaining length of each radial module is crimped around the circumference of the stent. The stent and the inflatable balloon are percutaneously introduced into a body lumen, following a previously positioned guidewire in an over-the-wire angioplasty catheter system, and tracked by a fluoroscope, until the balloon portion and associated stent are positioned within the body passageway at the point where the stent is to be placed. Thereafter, the balloon is inflated and the stent is expanded by the balloon portion from the collapsed diameter to a second expanded diameter. After the stent has been expanded to the desired final expanded diameter, the balloon is deflated and the catheter is withdrawn, leaving the stent in place. The stent may be covered by a removable sheath during delivery to protect both the stent and the vessels.

The expanded diameter is variable and determined by the desired expanded internal diameter of the body passageway. Accordingly, the controlled expansion of the stent is not likely to cause a rupture of the body passageway. Furthermore, the stent will resist recoil because the locking mechanism resists the sliding of the radial modules back to a more collapsed state. Thus, the expanded intraluminal stent will continue to exert radial pressure outward against the wall of the body passageway and will therefore, not migrate away from the desired deployment location.

From the foregoing description, it will be appreciated that a novel approach for expanding a lumen has been disclosed. While the components, techniques and aspects of the invention have been described with a certain degree of particularity, it is manifest that many changes may be made in the specific designs, constructions and methodology herein above described without departing from the spirit and scope of this disclosure.

While the number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A method for manufacturing a prosthesis comprising separate interlocking components, the method comprising:

fabricating from a material a contiguous one-piece blank comprising a first plane and a second plane and an intersection therebetween;

machining, by cutting or etching, in the first plane a pattern comprising a loop having a slide and lock structure therein, said pattern abutting the intersection at a location;

machining, by cutting or etching, a slot through the second plane at the location, said slot being configured to engage the slide and lock structure, wherein the first and second planes are joined by residual material along the intersection; and removing the residual material to separate the first and second planes, wherein the planes remain slideably coupled to one another.

2. The method of claim 1, wherein said contiguous one-piece blank comprises three or four intersecting planes, wherein each plane intersects two other planes.

3. The method of claim 1, wherein the material is selected from the group consisting of metal, ceramic, polymer, degradable material, and combinations thereof.

4. The method of claim 3, wherein said degradable material is selected from the group consisting of polyarylates (L-tyrosine-derived), free acid polyarylates, polycarbonates (L-tyrosine-derived), poly(ester-amides), lysine-containing poly(ester-amides), polyhydroxyalkanoates, poly(propylene fumarate-co-ethylene glycol) copolymer, polyanhydride esters, polyanhydrides, polyorthoesters, silk-elastin polymers, amino acid-containing polymers and corrodible calcium phosphate and magnesium alloys.

5. The method of claim 1, wherein the material further comprises a biologically responsive or physiologically active substance.

6. The method of claim 1, wherein the material is at least partially radiopaque.

* * * * *

UNITED STATES PATENT AND TRADEMARK OFFICE
CERTIFICATE OF CORRECTION

PATENT NO.   : 6,951,053 B2  
DATED        : October 4, 2005  
INVENTOR(S)  : Padilla et al.

It is certified that error appears in the above-identified patent and that said Letters Patent is hereby corrected as shown below:

<u>Title page,</u>
Item [54], Title, delete "METHOD OF MANUFACTURING A PROSTHESIS" and insert -- SLIDE AND LOCK STENT AND METHOD OF MANUFACTURE FROM A SINGLE PIECE SHAPE --.
Item [57], ABSTRACT,
Line 3, delete "signal" and insert -- single --.

<u>Column 2,</u>
Line 4, delete "therebetween" and insert -- there between --.

<u>Column 9,</u>
Line 11, delete "platium" and insert -- palladium --.

<u>Column 13,</u>
Line 11, delete "et aL" and insert -- et al. --.

<u>Column 18,</u>
Line 5, delete "therebetween" and insert -- there between --.

Signed and Sealed this

Sixteenth Day of May, 2006

JON W. DUDAS
*Director of the United States Patent and Trademark Office*